United States Patent [19]

Kantor

[11] Patent Number: 4,681,973

[45] Date of Patent: Jul. 21, 1987

[54] DIRECT N-ACYLATION OF AMINO ACIDS

[75] Inventor: Martin L. Kantor, Mamaroneck, N.Y.

[73] Assignee: USV Pharmaceutical Corporation, Fort Washington, D.C.

[21] Appl. No.: 833,706

[22] Filed: Feb. 27, 1986

[51] Int. Cl.[4] .......................................... C07C 125/06
[52] U.S. Cl. ..................................... 560/33; 548/341; 548/344; 548/495; 560/16; 560/29; 560/30; 560/148; 560/159; 560/160; 560/167
[58] Field of Search .................... 560/167, 16, 29, 30, 560/148, 159, 160, 33; 548/341, 344, 495

[56] References Cited

U.S. PATENT DOCUMENTS 3,769,271 10/1973 Southard ............................. 560/167

OTHER PUBLICATIONS

Fieser et al., (I), Reagents for Organic Synthesis, vol. 2 (1969) 426.

Fieser et al., (II), Reagents for Organic Synthesis, vol. 7 (1979) 383–384.

Primary Examiner—Michael L. Shippen

[57] ABSTRACT

Acylated amino acids having the general formula

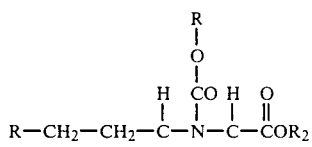

are prepared by reacting a compound of formula II

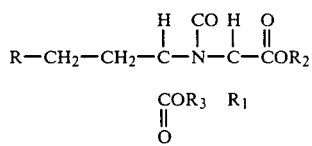

with a compound of formula III ROCOCl wherein R, $R_1$, $R_2$ and $R_3$ are as defined herein.

10 Claims, No Drawings

DIRECT N-ACYLATION OF AMINO ACIDS

BACKGROUND OF THE INVENTION

1. Field of the Invention

This invention relates to new chemical compounds useful as intermediates for the preparation of compounds having valuable pharmaceutical properties. The invention particularly relates to the preparation of N-substituted amino acid intermediates useful in the preparation of Angiotensin Converting Enzyme Inhibitor (ACEI) compounds and ACEI diuretics.

Synthesis of these novel intermediates is accomplished via a simple and unexpected process in which the amino acid is acylated directly on the nitrogen without first protecting the carboxylic acid moiety and subsequently deprotecting it. The acylated amino acid is obtained in good yield.

2. Description of the Prior Art

In the prior art of preparing peptides from amino acids, it is standard procedure to protect, and render inactive, all functionalities of a given amino acid which are not directly used in the coupling process. If reactive functionalities are allowed to remain, yield will be lower and purification made difficult because of the presence of large amounts of unwanted by-products from the interaction of these functionalities.

Two types of protecting groups are usually necessary in peptide synthesis:

the C-terminal protecting groups, those groups which render the acid portion of the amino acid inactive; and the N-terminal protecting groups, those groups which render the amine portion inactive.

After the coupling reaction of the amino acids to form the peptide chain, the terminals are deprotected.

Various compounds of the ACEI inhibitor type are prepared by this method, for example, compounds described in U.S. Pat. No. 4,496,541. Such synthesis, however, has its drawbacks notwithstanding its advantages. The steps required in protecting and deprotecting the functionalities in the amino acid renders the process rather lengthy, cumbersome and consequently expensive.

The present invention of acylating amino acids directly on the nitrogen without first protecting the carboxylic acid moiety and subsequently deprotecting it provides an elegant, clean and economically advantageous method of producing the intermediate compounds of the present invention.

SUMMARY

The present invention relates to the synthesis of compounds of the formula

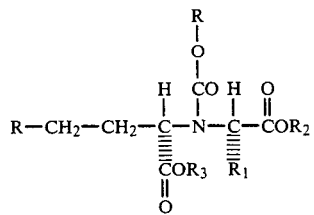

I by:

(a) reacting a compound of the formula

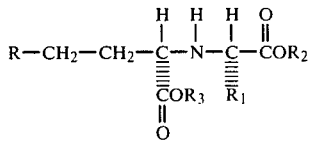

II with a compound of formula

ROCOCl    III in the reaction solvent methylene chloride under the reaction temperature of $-10°$ C. to $35°$ C. to obtain a reaction mixture;

(b) slowly adding pyridine to the reaction mixture to complete the reaction;

(c) washing the reaction mixture with dilute hydrochloric acid to remove pyridine and unreacted reactants;

(d) washing the reaction mixture with water to remove residual hydrochloric acid;

(e) separating the organic layer from the mixture and removing methylene chloride therefrom to obtain a solid residue;

(f) dissolving the residue in cyclohexane and allowing crystallization of the product; and (g) separating the crystals from cyclohexane;

wherein:

R is H, lower alkyl, aryl, aryl lower alkyl, hydroxy lower alkyl, dimethylamino lower alkyl, halo lower alkyl, imidazolyl lower alkyl, indolyl lower alkyl, mercapto lower alkyl, loweralkylthio lower alkyl, lower alkoxy, lower alkenoxy, di(lower alkyl)amino lower alkoxy, hydroxy lower alkoxy, acylamino lower alkoxy, acyloxy lower alkoxy, aryloxy, or aryloxy lower alkoxy;

$R_1$ is H, lower alkyl, aryl, aryl lower alkyl, hydroxy phenyl lower alkyl, hydroxy lower alkyl, acylamino lower alkyl, dimethylamino lower alkyl, halo lower alkyl, imidazolyl lower alkyl, indolyl lower alkyl, mercapto lower alkyl, or lower alkylthio lower alkyl; and $R_2$ and $R_3$ are independently H, lower alkyl, di(lower alkyl)amino, cycloalkyl, polycycloalkyl, cycloalkyl lower alkyl or aryl lower alkyl provided that at least one of $R_2$ and $R_3$ is hydrogen.

The alkyl groups per se or when present as substituents are preferably lower alkyl containing from 1 to 6 carbon atoms and may be straight or branched. These groups include methyl, ethyl, propyl, iso-propyl, butyl, isobutyl, amyl, hexyl and the like.

In the case of R the alkyl groups may carry substituents such as hydroxy, lower alkoxy, thio, di(lower alkyl)amino, halogen and nitro.

The cycloalkyl groups may be mono or polycyclic and contain from 3 to 20 carbons. These groups include cyclopropyl, cyclopentyl, cyclohexyl, cycloheptyl, bornyl, nor-bornyl, indanyl and the like. In the case of R these groups may be partially unsaturated and carry substituents such as halogen, hydroxy, lower alkyl, lower alkoxy, di(lower alkyl)amino, thiol, lower alkylmercapto, nitro, and trifluoromethyl.

The aryl groups contain from 6 to 10 carbon atoms and include such groups as phenyl or naphthyl and fused phenyl-cycloalkyl such as indanyl. In the case of R the aryl group may carry one or more substituents such as lower alkyl, lower alkenyl, lower alkynyl, hydroxy, lower alkoxy, di(lower alkyl)amino, thiol, lower alkylmercapto, hydroxy lower alkyl, thio lower alkyl, nitro, halogen, trifluoromethyl, methylene-dioxy or ureido.

The alkenyl and alkynyl groups when present as substituents preferably contain from 2 to 6 carbon atoms and may be straight or branched.

The halogen group may be fluorine, chlorine, bromine and iodine.

DETAILED DESCRIPTION OF THE INVENTION

An intermediate of particular interest is shown in formula IIIA, the synthetic process of which is depicted below:

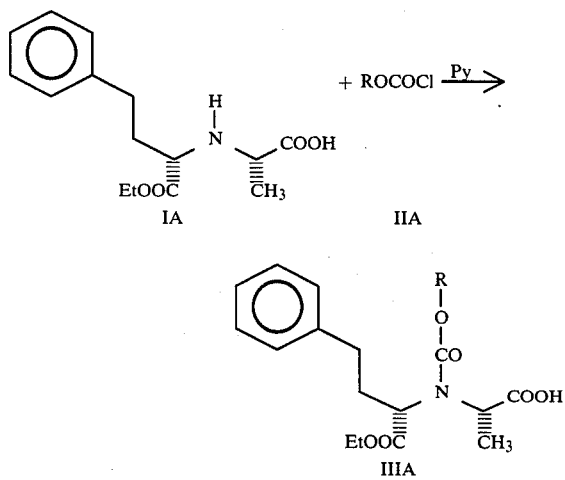

wherein R is 2,2,2-trichloroethyl.

The starting materials used in the present invention are commercially available and may also be prepared by known synthetic procedures. For starting materials according to formula I and IA, we prefer to use the naturally occurring amino acids which are commercially available. Examples of naturally occurring amino acids include: L-alanine, L-valine, L-leucine, L-isoleucine, L-phenylalanine, L-proline, L-serine, L-threonine, L-cysteine, L-cystine, L-methionine, L-tryptophan, L-tyrosine, L-asparagine, L-glutamine, L-aspartate, L-glutamate, L-lysine, L-arginine, L-histidine and the like.

The following examples will illustrate the process of the present invention.

EXAMPLE 1

N-[(1S)-1-Ethoxycarbonyl-3-Phenylpropyl]-N-(2,2,2-Trichloroethoxycarbonyl)-1-Alanine (IIIA)

In a 5 L flask, equipped with stirrer, thermometer, addition funnel, and cooling bath, 279 g (1M) of N-[(1S)-1-ethoxycarbonyl-3-phenylpropyl]-L-alanine (IA) was dissolved in 3 L of methylene chloride at about 20° C. While maintaining the temperature at about 20° C., 213.5 g (1.01M) of 2,2,2-trichloroethylchloroformate was added (IIA) over about 10 minutes. After this addition was completed, and while maintaining the temperature at about 20° C., 88 g (1.1M) of pyridine was added, in a steady stream, over about 15 minutes.

After the completion of the addition, the methylene chloride solution was washed with 500 ml of 7% hydrochloric acid, followed by two water washes of 500 ml each. The organic layer was transferred to a rotary evaporator. The methylene chloride was removed at 60° C. in vacuo. 500 ml of cyclohexane was added and the solvent was again removed at 60° C. in vacuo.

2 L of cyclohexane was added to the residue and warmed to dissolve. With stirring, the solution was cooled to about 20° C., seeded, and allowed to crystallize. The solution containing the crystals was then cooled to about 10° C., filtered, and washed with cold cyclohexane; dried in vacuo to obtain (IIIA) yield of 70% (stoichiometric) as white crystals melting at 75°–77° C.

EXAMPLE 2

N-α-[(1S)-1-(Ethoxycarbonyl)-ethyl]-N-α-2,2,2-Trichloroethoxy-Carbonyl-N-ε-Carbobenzyloxy-6-Lysine Dicyclohexylamine (S,S)

In a 50 ml flask, equipped with stirrer, thermometer, addition funnel, and cooling bath 3.9 g of N-α-[(1S)-1-(ethoxycarbonyl)-ethyl]-N-ε-carbobenzyloxy-L-lysine was dissolved in 30 ml of methylene chloride at about 20° C. The temperature was maintained at about 20° C. and 2.1 g of 2,2,2-trichloroethylchloroformate (II) was added over about 10 minutes. After this addition was complete, and while the temperature was maintained at about 20° C., 0.88 g of pyridine was added in a steady stream over about 15 minutes.

After the completion of the addition, the methylene chloride solution was washed with 5 ml of 7% hydrochloric acid, followed by two water washes of 5 ml each. The organic layer was transferred to a rotary evaporator. The methylene chloride was removed at 60° C. in vacuo. 5 ml of cyclohexane was added and again the solvent was removed at 60° C. in vacuo.

The dicyclohexylamine salt was prepared in isopropanol. The isolated salt had a melting point of 42°–45° C.

Comparative Example 3 shows that tetrahydrofuran, as the reaction solvent, functions less than satisfactorily.

COMPARATIVE EXAMPLE 3

N-[(1S)-1-Ethoxycarbonyl-3-Phenylpropyl]-N-(2,2,2-Trichloroethoxycarbonyl)-1-Alanine (IIIA)

Into a 50 ml flask, with stirrer, thermometer, cooling bath, addition funnel, 15 ml of tetrahydrofuran, and 2.8 g (0.01M) of N-[(1S)-1-ethoxycarbonyl-3-phenylpropyl]-L-alanine (IA) was charged. Keeping the temperature at about 0° C. 1.51 ml (0.011M) of 2,2,2-trichloroethylchloroformate (IIA) was added over about 15 minutes followed by 0.9 ml (0.011M) of pyridine over about 15 minutes. After the addition was completed, the sticky crystalline mass was filtered off, washed with a small amount of tetrahydrofuran and the filtrate was concentrated in vacuo.

Quantitative HPLC showed only about 30% yield and large amounts of impurities. The residue would not crystallize.

Comparative Example 4 shows that solvents, other than cyclohexane, are not suitable for effecting crystallization of the product.

COMPARATIVE EXAMPLE 4

N-[(1S)-1-Ethoxycarbonyl-3-Phenylpropyl]-N-(2,2,2-Trichloroethoxycarbonyl)-1-Alanine (IIIA)

Into a 50 ml flask, equipped with stirrer, thermometer, cooling bath, and addition funnel, 2.8 g (0.01M) of N-[(1S)-1-ethoxycarbonyl-3-phenylpropyl]-L-alanine (IA) and 10 ml of methylene chloride was charged. While maintaining the temperature at about 0° C., 1.55 ml (0.011M) of 2,2,2-trichloroethylchloroformate (IIA) was added, over about 15 minutes, and then 3 ml (0.02M) of triethylamine was added over about 20 minutes at the same temperature. The methylene chloride solution was washed with 2N hydrochloric acid, dried with anhydrous magnesium sulfate and concentrated to remove the methylene chloride. The hard glassy residue would not crystallize from any of the following solvents: heptane, ethyl acetate, ethyl acetate/heptane, acetone/water, methanol/water, isopropyl acetate.

Having described the invention, it will be apparent to one of ordinary skill in the art that changes and modifications can be made thereto without departing from the spirit and scope of the invention as set forth.

What is claimed is:

1. A process of preparing a compound of the formula

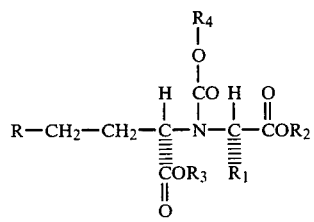

wherein:

R is H, lower alkyl, aryl, aryl lower alkyl, dimethylamino lower alkyl, halo lower alkyl, imidazolyl lower alkyl, indolyl lower alkyl, mercapto lower alkyl, lower alkoxy, lower alkenoxy, acylamino lower alkoxy, aryloxy, or aryloxy lower alkoxy;

$R_1$ is, lower alkyl, aryl, aryl lower alkyl, acylamino lower alkyl, imidazolyl lower alkyl, indolyl lower alkyl, mercapto lower alkyl, or lower alkylthio lower alkyl;

$R_2$ and $R_3$ are independently H, lower alkyl, di(lower alkyl)amino, cycloalkyl, polycycloalkyl, cycloalkyl lower alkyl or aryl lower alkyl provided that at least one of $R_2$ or $R_3$ is hydrogen, and $R_4$ is 2,2,2-trichloroethyl; comprising the steps of:

(a) reacting a compound of the formula:

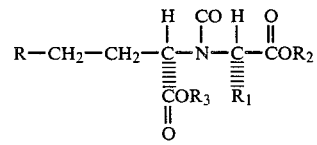

with a compound of formula:

   III wherein $R_1$, $R_2$, $R_3$ and $R_4$ denote a radical group as defined above, in the reaction solvent methylene chloride;

(b) completing the reaction by the addition of pyridine;
(c) washing the reaction mixture with hydrochloric acid;
(d) washing the reaction mixture with water;
(e) separating the organic solvent from the mixture and obtaining a solid residue;
(f) dissolving said solid residue in cyclohexane;
(g) crystallizing the dissolved residue; and
(h) separating the so obtained crystals from cyclohexane.

2. The process of claim 1 wherein said compound II is reacted with said compound III in the solvent methylene chloride at the reaction temperature of $-10°$ C.-35° C.

3. The process of claim 1 wherein the organic layer comprising methylene chloride is separated from the solid residue by vacuum.

4. The process of claim 1 further comprising: washing the solid residue obtained in step (e) with cyclohexane and removing said cyclohexane from said residue under vacuum.

5. The process of claim 1 wherein said separation of crystals from said cyclohexane is by filtration.

6. A process of preparing a compound of the formula

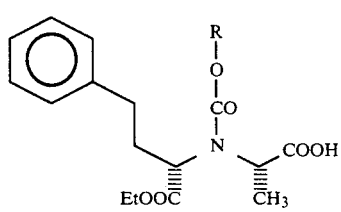

comprising the steps of:

(a) reacting a compound of the formula

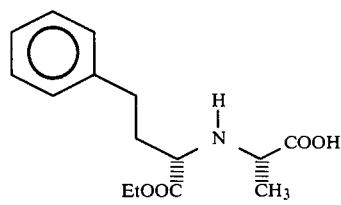

with a compound of formula

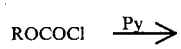   IIA wherein R is 1,1,1-trichloroethyl, in the reaction solvent methylene chloride;
(b) completing the reaction by the addition of pyridine;
(c) washing the reaction mixture with hydrochloric acid;
(d) washing the reaction mixture with water;
(e) separating the organic solvent from the mixture and obtaining a solid residue;
(f) dissolving said solid residue in cyclohexane;
(g) crystallizing the dissolved residue; and
(h) separating the so obtained crystals from cyclohexane.

7. The process of claim 6 wherein said compound II is reacted with said compound III in the solvent methylene chloride at the reaction temperature of $-10°$ C.-35° C.

8. The process of claim 6 wherein the organic layer comprising methylene chloride is separated from the solid residue by vacuum.

9. The process of claim 6 further comprising: washing the solid residue obtained in step (e) with cyclohexane and removing said cyclohexane from said residue under vacuum.

10. The process of claim 6 wherein said separation of crystals from said cyclohexane is by filtration.

* * * * *